United States Patent [19]

Taylor

[11] Patent Number: 5,304,185

[45] Date of Patent: Apr. 19, 1994

[54] NEEDLE HOLDER

[75] Inventor: Charles S. Taylor, San Francisco, Calif.

[73] Assignee: Unisurge, Inc., Cupertino, Calif.

[21] Appl. No.: 971,279

[22] Filed: Nov. 4, 1992

[51] Int. Cl.⁵ ........................................... A61B 17/00
[52] U.S. Cl. .................................. 606/147; 606/148; 606/207; 606/208
[58] Field of Search ............... 606/144, 147, 139, 148, 606/150, 207, 208, 205

[56] References Cited

U.S. PATENT DOCUMENTS

| | | | |
|---|---|---|---|
| 695,292 | 3/1902 | Ermold | 606/147 |
| 1,704,992 | 3/1929 | St. Elmo Sanders | 606/147 |
| 1,918,889 | 7/1933 | Bacon | 606/207 |
| 5,100,421 | 3/1992 | Christoudias | 606/147 |

OTHER PUBLICATIONS

Karl Storz, "Szabo-Berci Needle Driver Set," *Contemporary Surgery*, Oct. 1992, vol. 41, p. 88.

*Primary Examiner*—Tamara L. Graysay
*Attorney, Agent, or Firm*—Flehr, Hohbach, Test, Albritton & Herbert

[57] ABSTRACT

Needle holder having an elongate tubular member serving as a shaft and having a bore extending therethrough and having proximal and distal extremities. A push-pull rod is slidably mounted in the bore in the tubular member and has proximal and distal extremities. First and second jaws are carried by the distal extremity of the elongate tubular member. The first jaw is secured to the distal extremity of the tubular member in a fixed position. The second jaw is connected to the push-pull rod to cause the second jaw carried thereby to be moved between a closed needle-clamping position and an open position upon relative movement between said push-pull rod and said tubular member. One of said first and second jaws consists of first and second jaw portions having a slot extending therebetween. The other of said first and second jaws overlies and is disposed in the slot. An actuation device is secured to the tubular member and to the push-pull rod for causing the relative movement between the push-pull rod and the tubular member.

17 Claims, 2 Drawing Sheets

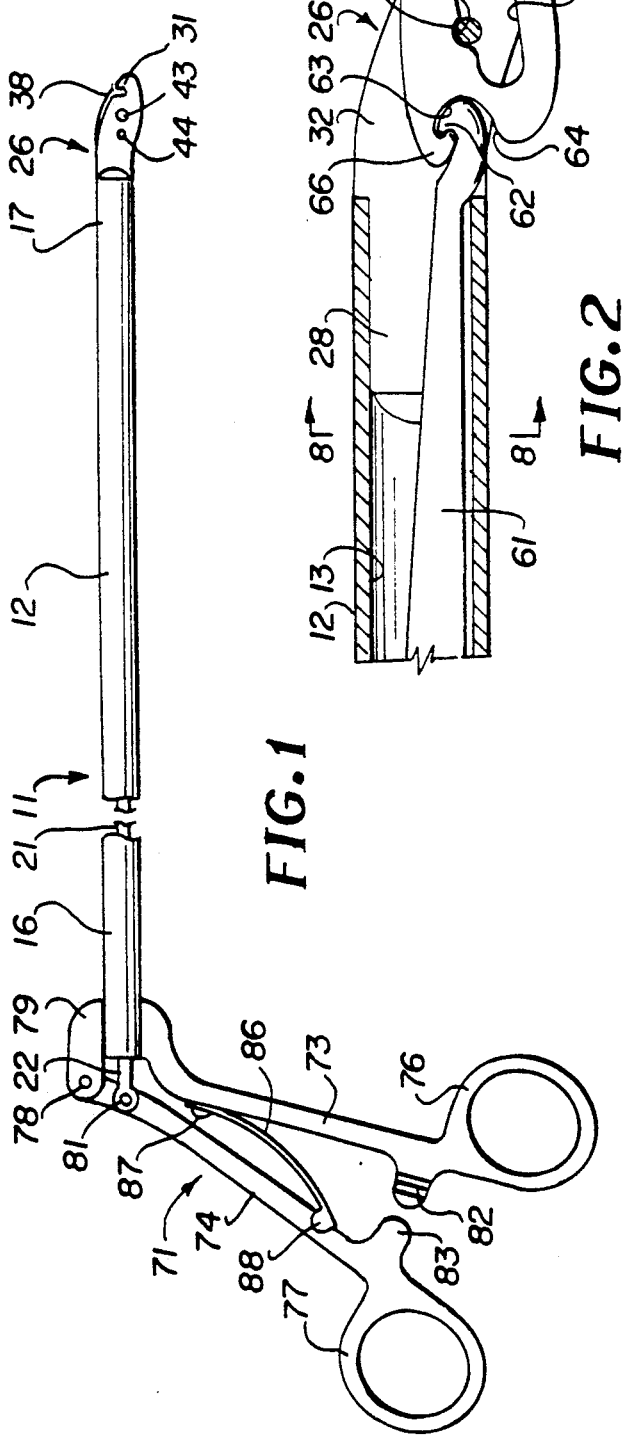
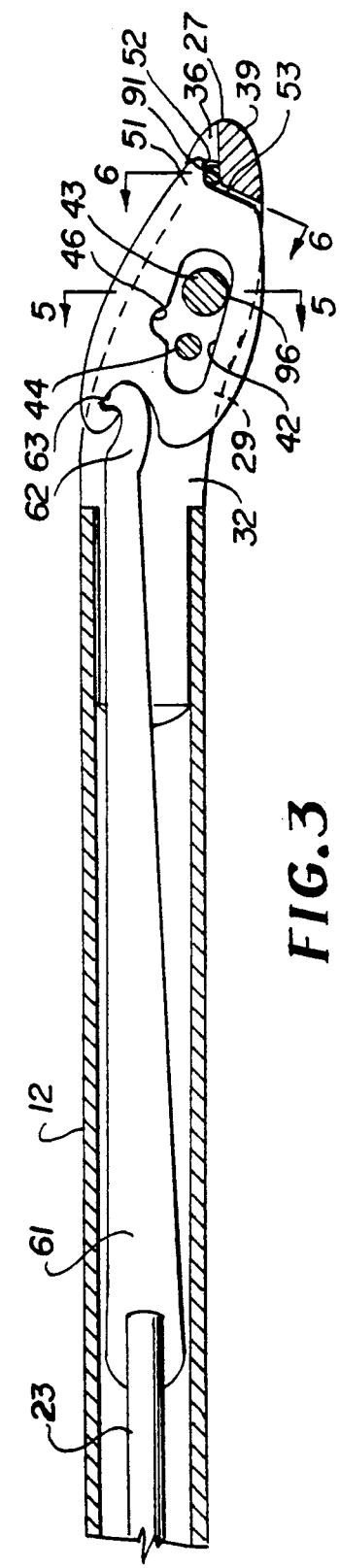
FIG. 1
FIG. 2
FIG. 3

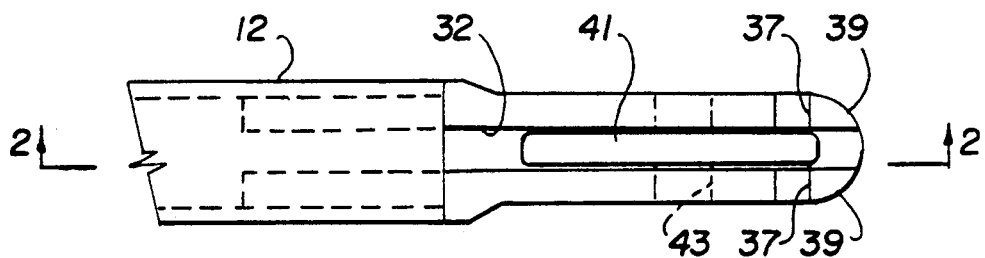
FIG. 4
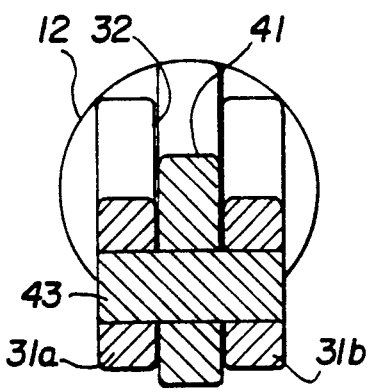
FIG. 5
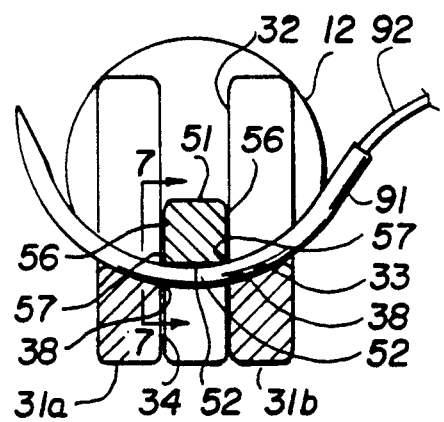
FIG. 6
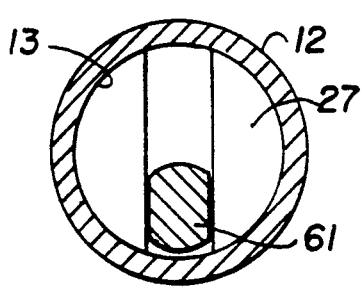
FIG. 8
FIG. 7

NEEDLE HOLDER

This invention relates to a needle holder and more particularly to an endoscopic needle holder which holds the needle very firmly and which can be used in laparoscopic procedures.

Needle holders have heretofore been provided. However, typically such needle holders have the disadvantage in that the needles held thereby have a tendency to turn or rotate when needed. There is therefore a need for a new and improved needle holder which will firmly grip the needle to prevent rotation or turning of the same.

In general, it is an object of the present invention to provide an endoscopic needle holder which firmly grips the needle to prevent rotation or turning of the same.

Another object of the invention is to provide a needle holder of the above character which is particularly adaptable for use in laparoscopic procedures.

Another object of the invention is to provide a needle holder which can be readily operated by one hand.

Additional objects and features of the invention will appear from the following description in which the preferred embodiments are set forth in detail in conjunction with the accompanying drawings.

FIG. 1 is a side elevational view of an endoscopic needle holder incorporating the present invention.

FIG. 2 is an enlarged cross-sectional view of the distal extremity of the needle holder shown in FIG. 1 with the jaws in an open position and also taken along the line 2—2 of FIG. 4.

FIG. 3 is a side elevational view in cross section of the distal extremity of the endoscopic needle holder shown in FIG. 1 showing the jaws in a closed position and clamping a needle therebetween.

FIG. 4 is a top plan view of the distal extremity of the endoscopic needle holder shown in FIG. 1.

FIG. 5 is a cross-sectional view taken along the line 5—5 of FIG. 3.

FIG. 6 is a cross-sectional view taken along the line 6—6 of FIG. 3.

FIG. 7 is a cross-sectional view looking along the line 7—7 of FIG. 6.

FIG. 8 is a cross-sectional view taken along the line 8—8 of FIG. 2.

In general the needle holder is comprised of an elongate tubular member serving as a shaft and having a bore extending therethrough and having proximal and distal extremities. A push-pull rod is slidably mounted in the bore in the tubular member and has proximal and distal extremities. First and second jaws are carried by the distal extremity of the elongate tubular member. Means is provided for securing the first jaw to the distal extremity of the tubular member in a fixed position. Means is provided for connecting said second jaw to said push-pull rod to cause the second jaw carried thereby to be moved between a closed needle-clamping position and an open position upon relative movement between the push-pull rod and the tubular member. One of said first and second jaws consist of first and second jaw portions having a slot extending therebetween. The other of said first and second jaws overlies and is disposed in said slot. Actuation means is provided which is secured to the tubular member and to the push-pull rod for causing said relative movement between the push-pull rod and the tubular member.

In general, the endoscopic needle holder incorporating the present invention is comprised of an elongate tubular member serving as a shaft having a passage extending therethrough and having proximal and distal extremities. A push-pull rod is slidably mounted in the passage in the tubular member and also has proximal and distal extremities. First and second jaws are carried by the distal extremity o of the elongate member. Means is provided for securing the first jaw to the distal extremity of the tubular member in a fixed position. A cam member is provided which has an elongate slot therein. Means is provided for securing the second jaw to said cam member. A pivot pin is secured to the first jaw and extends through the elongate slot. A guide pin is secured to the first jaw and is spaced from the pivot pin and also extends through the elongate slot. A recess is formed in said cam member which is adapted to receive the stop pin and opens into the elongate slot. Means is provided for connecting the cam member to the push-pull rod so that the cam member can be shifted from a position in which the second jaw is in an open position with respect to the first jaw and said pivot pin is disposed in one end of said slot and said guide pin is disposed in said recess and in a position in which said second jaw is in a clamping closed position with respect to said first jaw and in which the distal extremity of the elongate slot in the cam member is disposed distally of the pivot pin and said guide pin is out of engagement with said recess as said push-pull rod is moved relative to said tubular member. Handle means is provided adapted to be grasped by the human hand and secured to the tubular member and to said push-pull rod for causing relative movement between push-pull rod and the tubular member.

More particularly, as shown in the drawings, an endoscopic needle holder 11 incorporating the present invention consists of a tubular member 12 formed of a suitable material such as stainless steel or brass or a composite material which is provided with a bore or passage 13 extending therethrough. It has proximal and distal extremities 16 and 17. A push-pull rod 21 formed of a suitable material such as brass or stainless steel is disposed within the bore 13. It is provided with proximal and distal extremities 22 and 23.

Needle holding means 26 is carried by the distal extremity 17 of the tubular member 12. The needle holding means 26 consists of a nosepiece 27 formed of a suitable material such as stainless steel and which is provided with a cylindrical proximal portion 28 which is mounted in the bore 13 in the distal extremity of the tubular 12, as shown particularly in FIGS. 2 and 3, and can be retained therein by a suitable manner, as for example by brazing. The nosepiece 27 has a forward or distal extremity 29 which is generally rectangular in cross-section and depends downwardly from the longitudinal axis of the tubular member 12 as shown in FIGS. 1, 2 and 3 of the drawings. The forward or distal extremity 29 is provided with a first or lower jaw 31 which has a vertically extending slot 32 extending through the same to form jaw portions 31a and 31b on opposite sides of the same. The portions 31a and 31b have horizontally disposed aligned arcuate jaw surfaces 33 (see FIG. 6) which extend in directions which are perpendicular to and parallel to the longitudinal axis of the tubular member 12. The surfaces 33 are adjoined by surfaces 34 (see FIG. 2) provided on upstanding hook portions 36 formed integral with the first or lower jaw portions 31a and 31b. The surfaces 34 extend at right angles to the surfaces 33 and form upwardly extending U-shaped recesses 37 in the jaw portions 31a and 31b (as shown particularly in FIGS. 2 and 4). The surfaces 33 form sharp corners 38 (see FIG. 6) on opposite sides of the slot 32 for a purpose hereinafter described. As can be seen from FIGS. 2 and 3 of the drawings, the distal extremities of the nose portions 31a and 31b are provided with rounded surfaces 39.

A generally oval-shaped cam member 41 is vertically disposed within the slot 32. The cam member 41 is provided with slot 42 extending along the major axis of the oval-shaped cam member 41. A pivot pin 43 has been mounted in the first or lower jaw 31 and extends between the jaw portions 31a and 31b, and extends through the elongate slot 42 provided in the cam member 41. As can be seen, the slot elongate 42 has a width which is only slightly greater than the diameter of the pivot pin 43. The elongate slot 42 is provided with proximal and distal extremities in which the distal extremity is in the form of a semicircle which corresponds generally to the circumference of the pivot pin 43. A guide pin 44 of a smaller diameter than the pivot pin 43 is mounted in the first or lower jaw 31 and also extends from the jaw portions 31a and 31b across the slot 32 and through the elongate slot 42 in the cam member 41. The cam member 41 is provided with a recess 46 therein which is substantially semicircular and which has a diameter which is only slightly greater than that of the guide pin 44. The recess 46 opens up into the elongate slot 42 and is adapted to receive the guide pin 44 in a manner hereinafter described.

The guide pin 44 is spaced from the pivot pin 43 and is in general alignment with the downwardly depending forward extremity 29 of the nosepiece 27.

A second or upper jaw 51 is provided. Means is provided for securing the second or upper jaw 51 to the cam member 41, and as shown can take the form of the second or upper jaw 51 being formed integral with the cam member 41 and protruding distally therefrom. The second or upper jaw 5 is provided with a planar jaw surface 52. The longitudinal axis of the elongate slot 42 extends at a small angle with respect to the planar surface 52. By way of example, this small angle can range from 5° to 30°, and preferably is an angle of approximately 20° for a purpose hereinafter described. The jaw surface 52 extends at approximately a right angle to a surface 53 provided on the cam member 41 to provide an L-shaped recess 54. The second or upper jaw is provided with surfaces 56 which extend at right angles to the jaw surface 52 and form substantially right angle sharp corners 57 (see FIG. 6) for a purpose hereinafter described.

Means is provided for forming a rocking-type connection between the push-pull rod 21 and the cam member 41 and for causing movement of the second or upper jaw 51 from an open to a closed position with respect to the first or lower jaw 31. Such means consists of an elongate lever arm link 61 which has its proximal extremity secured to the distal extremity of the push-pull rod 23 by suitable means such as brazing. The lever arm link 61 can be substantially rectangular in cross-section as shown in FIG. 8, and has a hook 62 formed on its distal extremity which is provided with a rounded surface 63 that is adapted to seat within an arcuate recess 64 provided in the cam member 41 proximal of the elongate slot 42 and in which the hook 66 formed as part of the cam member engages the hook 62 of the link 61.

Actuator means 71 is provided for causing relative movement between the push-pull rod 21 and the tubular member 12. Such actuator means as shown in the drawings is in the form of handle means adapted to be grasped by the human hand and consists of first and second handle members 73 and 74 provided with finger loops 76 and 77. The handle member 73 is secured in a fixed position to the proximal extremity 16 of the tubular member 12 by suitable means such as brazing. The handle member 74 is pivotally connected by a pin 78 to a bracket 79 that is fixed to the proximal extremity 16 of the tubular member 12 immediately above the handle member 73 by suitable means such as brazing. The handle member 74 is also pivotally connected to the push-pull rod 22 by a pin 81. It should be appreciated that other actuator means other than the handle means disclosed can be used for causing the relative motion such as an Serrated latching means is provided as a part of the handle means 71 and consists of serrated tabs 82 and 83 provided on the handle members 73 and 74 which are adapted to latch to each other when brought into registration so that the second or upper jaw 51 is retained in a closed position with respect to the first or lower jaw 31. Yieldable spring means is provided to prevent inadvertent engagement of the latching means and consists of a leaf spring 86 which is secured to the handle member 73 by a rivet 87 and which has the other end provided with a U-shaped member 88 engaging the handle member 74.

Operation and use of the endoscopic needle holder 11 may now be briefly described as follows. Let it be assumed that the needle holder 11 is to be used in a laparoscopic procedure and that a laparoscopic procedure is being performed in the abdomen of a patient and that one or more cannulas have been introduced into the abdomen of the patient. Also let it be assumed that a surgical procedure is being performed in the abdominal cavity of the patient and that it is now desired to close with a suture. Also let it be assumed that a conventional curved surgical needle 91 carrying a suture 92 has been introduced through one of the cannula in the abdominal cavity into the region where the suturing is to take place. Such a conventional needle 91 is typically provided with flats 93 which extend in a direction which is parallel to the axis of curvature of the needle 91. The surgeon then takes the endoscopic needle holder of the present invention and grasps the same by the fingers of the hand extending through the finger loops 76 and 77 and directing the shaft formed by the tubular member 12 to advance the needle holding means 26 through the cannula. While observing the interior of the abdominal cavity through an endoscope provided through another cannula, the physician opens the jaws 51 and 31 to the open position shown in FIG. 2 by separating the finger loops 76 and 77 to cause the push-pull member 23 to be pulled proximally and to carry with it the link 61 to pull on the interlocking hooks 62 and 66 to move the second or upper movable jaw 51 to an open position with respect to the first or lower jaw 31. Upon initial movement of the link 61, the cam member 41 is moved so that the forward extremity of the elongate slot 42 is abutted in engagement with the pivot pin 43. The continued rearward or pulling movement of the link 6 causes the proximal extremity of the cam member to be cammed downwardly from the position shown in FIG. 3 to the position shown in FIG. 2 and to cause the guide pin 44 to enter the recess 46 to assure that the movable jaw moves downwardly before moving forwardly. With the jaws in an open position, the endoscopic needle holder 11 can be manipulated within the abdominal cavity to grasp the needle 91 previously positioned therein.

As soon as the needle has been positioned within the rectangular U-shaped recesses 38 in the jaw portions 31a and 31b, the surgeon utilizes the fingers of the hand to bring the finger loops 76 and 77 towards each other to cause pushing movement on the push-pull rod 23 and the link to cause the proximal extremity of the cam member to be rocked upwardly and forwardly until the cam member 41 is released from the guide pin 44 and then causing the cam member 4 to move forwardly at a slightly inclined angle to move the upper jaw 51 in a downward direction as viewed in FIG. 2 until the jaw 51 engages the needle 91 in the recess 54. The jaw 51 continues to move downwardly and forwardly so that the flats 93 of the needle 91 are firmly clamped in the recesses 37 and 54 of the jaws 51 and 31 (see FIG. 7). The squarish shapes of the jaws 51 and 31 create a very strong clamping force downwardly as well as in a longitudinal direction on the needle to cause the needle to be held very firmly between the jaws. As hereinbefore described, sharp corners 38 and right-angle corners 57 are provided which firmly grip the needle as shown in FIG. 6. The corners make a four-point contact with the needle, with the two corners 57 of the upper jaw 51 making contact with one side of the needle and the corners 38 of the lower jaw portions 31a and 31b making contact with the flat 93 on the opposite side of the needle (see FIG. 7). The forces created by these corners serve to create a slight bending deformation of the needle to occur within its elastic limits. Thus, the needle 91 acts as a spring resisting these bending moments to ensure that the needle 91 is firmly retained therein and cannot be rotated or turned during the suturing procedure.

Because of the mechanical advantage provided by the endoscopic needle holder, a small amount of force, as for example 1 pound applied to the handle means by the fingers, can apply 20 to 30 times this amount of force at the needle. The handle members 72 and 73 provide a first mechanical advantage of approximately 4-to-1. This mechanical advantage is compounded by the mechanical advantage provided by the cam member acting upon the upper jaw 51. Thus, since a relatively small angle is provided during movement of the cam member in a forward and downward direction carrying with it the jaw 51, a large mechanical advantage, as for example 6-to-1 can be readily obtained, to provide in total a mechanical advantage of approximately 24. It is this unique mechanical advantage in conjunction with the gripping action provided by the jaws 31 and 51 that firmly grips the needle within the needle holder and prevents rotation or turning of the same so that the surgeon can readily manipulate the needle by merely appropriately manipulating the handle means 71.

This retention force on the needle 91 is augmented by the extreme frictional force between the pivot pin 43 and the interior surface of the slot 42 at point 96. Rotational movement of the handle means causes the needle to enter the tissue through which a suture is to be made. The suturing 30 of the incision can be completed in the manner described in co-pending application Ser. No. 07/971,896, filed Nov. 4, 1992 and knots tied in the sutures. The endoscopic needle holder 11 can be utilized to manipulate the needle 91 in the manner desired to complete suturing of the incision. For example, the needle can be introduced through the tissue and then released and then grasped again on the other side of the tissue to continue and then complete the suturing operation.

It is apparent from the foregoing that there has been provided an endoscopic needle holder which provides large retention forces to firmly grip the needle so that the surgeon can accomplish precise suturing operations without any danger of rotation or turning in the needle holder. Although one specific mechanism has been disclosed for providing the large mechanical advantage utilized in the needle holder of the present invention, other mechanisms utilizing the same principles can be provided within the scope of the present invention. Also although the needle holder has been described principally in conjunction with endoscopic procedures, it should be appreciated that it can be used in non-endoscopic surgical procedures. Also it can be used for grasping items other than needles if desired.

What is claimed is:

1. In a needle holder for use with a curved surgical needle, an elongate tubular member serving as a shaft having a bore extending therethrough and having proximal and distal extremities, a push-pull rod slidably mounted in the bore in the tubular member and having proximal and distal extremities, first and second jaws carried by the distal extremity of the elongate tubular member, means securing the first jaw to the distal extremity of the tubular member in a fixed position, means connecting said second jaw to said push-pull rod to cause the second jaw carried thereby to be moved between a closed needle-clamping position and an open position upon relative movement between said push-pull rod and said tubular member, one of said first and second jaws consisting of first and second jaw portions having a slot extending therebetween, said first and second jaw portions having arcuate needle-engaging surfaces which in cross-sections conform to the curvature of curved surgical needle, the other of said first and second jaws overlying and being disposed in said slot and having first and second corners in close proximity to the arcuate needle engaging surfaces of the first and second jaw portions and actuation means secured to said tubular member and to said push-pull rod for causing said relative movement between the push-pull rod and the tubular member.

2. A needle holder as in claim 1 wherein said first and second jaw portions are provided with sharp corners adapted to engage the curved surgical needle.

3. A needle holder as in claim 2 wherein said first and second corners are substantially right angle corners adapted to engage the curved surgical needle.

4. A needle holder as in claim 1 wherein said actuation means is in the form of scissors-type handles.

5. A needle holder as in claim 1 wherein said jaw portions are secured to said tubular member.

6. A needle holder as in claim 1 together with hook means carried by the first and second jaw portions.

7. In a needle holder adapted to be used by the human hand, an elongate tubular member serving as a shaft having a bore extending therethrough and having proximal and distal extremities, a push-pull rod slidably mounted in the bore in the tubular member and having proximal and distal extremities, first and second jaws carried by the distal extremity of the elongate tube member, means securing the first jaw to the distal extremity of the tubular member in a fixed position, a cam member having an elongate slot therein, means securing said second jaw to said cam member, a pivot pin secured to said first jaw and extending through said elongate slot in the cam member, means connecting said cam member to said push-pull rod for causing the cam member to be shifted with respect to said pivot pin to cause the second jaw carried thereby to be moved between a closed needle-clamping position and an open position as said push-pull rod is moved relative to said tubular member by causing rocking movement of said cam member with respect to the pivot pin, and handle means adapted to be grasped by the human hand and secured to said tubular member and said push-pull rod for causing said relative movement between the push-pull rod and the tubular member.

8. A needle holder as in claim 7 together with a guide stop pin secured to said first jaw and extending through said cam member, wherein said cam member has a recess formed therein adapted to receive said guide pin.

9. A needle holder as in claim 8 wherein said guide pin is spaced proximally of the pivot pin.

10. A needle holder as in claim 7 together with hook means carried by the fixed jaw.

11. A needle holder as in claim 7 wherein said means connecting said cam member to said push-pull rod includes first and second interconnecting hook members permitting a rocking movement of said cam member with respect to said push-pull rod.

12. A needle holder as in claim 7 wherein said first jaw secured to the tubular member consists of first and second jaw portions having a slot extending therebetween, and wherein said second jaw overlies said slot.

13. A needle holder as in claim 12 wherein said first and second jaw portions are provided with sharp corners adapted to engage a needle.

14. A needle holder as in claim 13 wherein said second jaw is provided with first and second right angle corners adapted to engage a needle.

15. A needle holder as in claim 7 wherein said handle means is in the form of scissors-type handles.

16. A needle holder as in claim 7 wherein said means connecting said cam member to said push-pull rod includes a link interconnecting said push-pull and said cam member.

17. A needle holder as in claim 16 wherein said means connecting said cam member to said push-pull rod also includes interconnecting hook portions connecting said link and said cam member to permit rocking movement of the cam member about the pivot pin.

* * * * *